United States Patent [19]

Sun et al.

[11] Patent Number: 5,334,736
[45] Date of Patent: Aug. 2, 1994

[54] FUNCTIONALIZING CARBOHYDRATE DERIVATIVES BY BASE-INDUCED β-ELIMINATIOM FORMING BIOACTIVE DERIVATIVES CONTAINING HYDROXY-DIENE SUBUNITS

[75] Inventors: Lumin Sun, Plano; John R. Falck, Dallas, both of Tex.

[73] Assignee: University of Texas System Board of Regents, Austin, Tex.

[21] Appl. No.: 701,655

[22] Filed: May 16, 1991

[51] Int. Cl.$^5$ .............................................. C07C 51/00
[52] U.S. Cl. ................................. 554/148; 554/124; 536/18.5; 536/18.6
[58] Field of Search ............... 260/413; 654/127, 124; 554/148; 536/185, 186

[56] References Cited

PUBLICATIONS

Maehr et al, Journal of Organic Chemistry, vol. 53, 1988, pp. 832–836.

*Primary Examiner*—José G. Dees
*Assistant Examiner*—Deborah D. Carr
*Attorney, Agent, or Firm*—H. Dale Langley, Jr., Johnson & Gibb

[57] ABSTRACT

A method to functionalize carbohydrate derivatives by base-induced β-elimination and subsequent olefination to form biologically active products containing α-hydroxy-diene or α,β-dihydroxy-diene subunits. Also disclosed are methods to prepare biologically active derivatives of fatty acids containing α-hydroxy-diene groups and α,β-dihydroxy-diene groups from derivatives of 2-deoxyfuranoses and derivatives of 2-deoxypyranoses, respectively.

24 Claims, 13 Drawing Sheets

A = organometallic reagent of tin, lithium, cerium, cesium, copper (I), copper (II), titanium, magnesium, and silicon (BuLi, $C_uC_5H_{11}$, CuLi ($\diagup\!\!\!\diagdown\!C_5H_{11}$)$_2$, CuLiBu$_2$, CuLi($C_5H_{11}$)$_2$, $C_5H_{11}$MgX, BuMgX); Wittig reagent (BrPh$_3$PC$_6$H$_{13}$); anions (α-sulfonyl, α-cyano, α-nitro and vinylogous analogs ($\diagup\!\!\!\diagdown\!\!\stackrel{Li}{\diagdown}\!\!SO_2Ph$, $\diagup\!\!\!\diagdown\!\!\stackrel{Li}{\diagdown}\!CN$, $\diagup\!\!\!\diagdown\!\!\stackrel{Li}{\diagdown}\!NO_2$ )); Peterson olefination reagent; or enolate (aldehyde, ketone, lactone enolate, and vinylogous analogs ($\diagup\!\!\!\diagdown\!\!\stackrel{O}{\diagdown}\!Li$, $Li\!\diagdown\!\!\stackrel{O}{\diagup}\!O$ ))

B = organometallic reagent of lithium and magnesium; anions (α-sulfonyl, α-cyano, α-nitro and vinylogous analogs ($\diagup\!\!\!\diagdown\!\!\stackrel{Li}{\diagdown}\!SO_2Ph$, $\diagup\!\!\!\diagdown\!\!\stackrel{Li}{\diagdown}\!CN$, $\diagup\!\!\!\diagdown\!\!\stackrel{Li}{\diagdown}\!NO_2$ )); or enolate (aldehyde, ketone, lactone enolate, and vinylogous analogs ($\diagup\!\!\!\diagdown\!\!\stackrel{O}{\diagdown}\!Li$, $Li\!\diagdown\!\!\stackrel{O}{\diagup}\!O$ )). More preferably: Wittig reagent (BrPh$_3$P$\diagup\!\!\!\diagdown\!=\!\diagup\!\!\!\diagdown$COOMe, BrPh$_3$P$\diagup\!\!\!\diagdown\!=\!\diagup\!\!\!\diagdown$COOMe, BrPh$_3$PC$_8$H$_{17}$COOH); or Petersons olefination reagent (organosilyl regents).

R$_A$ = the organic moiety after coupling of A

R$_B$ = the organic moiety after coupling of B

*FIG. 1A*

$Z = O; S; NR_2$ $R$ = alkyl (Me, Et, t-Bu, ArCH$_2$, i-Pr, Ph$_3$C, THP); aryl (Ph, 4-NO$_2$C$_6$H$_4$, 4-MeOC$_6$H$_4$); acyl (CH$_3$-CO-, Ph-CO-, Ph-CO-CH$_2$, X$_3$C-CO-); or silyl (trialkylSi, t-BuPh$_2$Si) group $R_1$ = alkyl (Me, Et, t-Bu, ArCH$_2$, i-Pr, Ph$_3$C, THP); acyl (Ph-CO-, Ac, pivaloate, X$_3$C-CO-); sulfonate (Ts, mesylate, triflate); or silyl (trialkylSi, t-BuPh$_2$Si) group $R_2$ = (CH$_2$)$_n$-OR$_1$ and n=1-10; carbonyl ((CH$_2$)$_n$ CHO and n=0-10); halides (C$_n$H$_{2n}$X and X=Cl, Br, I, and n=1-10); alkyne (C$_n$H$_{2n-3}$ and n=2-10); alkene (C$_n$H$_{2n-1}$ and n=2-10); alkane (C$_n$H$_{2n+1}$ and n=1-10)

*FIG. 1B*

A = organometallic reagent of tin, lithium, cerium, cesium, copper (I), copper (II), titanium, magnesium, and silicon (BuLi, $C_u C_5 H_{11}$, CuLi ($\diagup\!\!\!\!\diagdown_{C_5H_{11}}$)$_2$, CuLiBu$_2$, CuLi(C$_5$H$_{11}$)$_2$, C$_5$H$_{11}$MgX, BuMgX); Wittig reagent (BrPh$_3$PC$_6$H$_{13}$); anions (α-sulfonyl, α-cyano, α-nitro and vinylogous analogs (⁀⁀⁀$^{Li}$SO$_2$Ph, ⁀⁀⁀$^{Li}$CN, ⁀⁀⁀$^{Li}$NO$_2$ )); Peterson olefination reagent; or enolate (aldehyde, ketone, lactone enolate, and vinylogous analogs (⁀⁀⁀$^O$Li, Li-$^O$⌬$_O$ ))

B = organometallic reagent of lithium and magnesium; anions (α-sulfonyl, α-cyano, α-nitro and vinylogous analogs (⁀⁀⁀$^{Li}$SO$_2$Ph, ⁀⁀⁀$^{Li}$CN, ⁀⁀⁀$^{Li}$NO$_2$ )); or enolate (aldehyde, ketone, lactone enolate, and vinylogous analogs (⁀⁀⁀$^O$Li, Li-$^O$⌬$_O$ )). More preferably: Wittig reagent (BrPh$_3$P⁀⁀=⁀⁀COOMe, BrPh$_3$P⁀⁀=⁀⁀COOMe, BrPh$_3$PC$_8$H$_{17}$COOH); or Petersons olefination reagent (organosilyl reagents).

R$_A$ = the organic moiety after coupling of A

R$_B$ = the organic moiety after coupling of B

*FIG. 2A*

$Z = O; S; NR_2$ $R = $ alkyl (Me, Et, t-Bu, ArCH$_2$, i-Pr, Ph$_3$C, THP); aryl (Ph, 4-NO$_2$C$_6$H$_4$, 4-MeOC$_6$H$_4$); acyl (CH$_3$-CO-, Ph-CO-, Ph-CO-CH$_2$, X$_3$C-CO-); or silyl (trialkylSi, t-BuPh$_2$Si) group $R_1 = $ alkyl (Me, Et, t-Bu, ArCH$_2$, i-Pr, Ph$_3$C, THP); acyl (Ph-CO-, Ac, pivaloate, X$_3$C-CO-); sulfonate (Ts, mesylate, triflate); or silyl (trialkylSi, t-BuPh$_2$Si) group $R_2 = $ (CH$_2$)$_n$-OR$_1$ and n=1-10; carbonyl ((CH$_2$)$_n$ CHO and n=0-10); halides (C$_n$H$_{2n}$X and X=Cl, Br, I, and n=1-10); alkyne (C$_n$H$_{2n-3}$ and n=2-10); alkene (C$_n$H$_{2n-1}$ and n=2-10); alkane (C$_n$H$_{2n+1}$ and n=1-10)

*FIG. 2B*

C = organometallic reagent of tin, lithium, cerium, cesium, copper (I), copper (II), titanium, magnesium, and silicon (BuLi, CuC$_5$H$_{11}$, CuLi(⌐\C$_5$H$_{11}$)$_2$, CuLiBu$_2$, CuLi(C$_5$H$_{11}$)$_2$, C$_5$H$_{11}$MgX, BuMgX); Wittig reagent (BrPh$_3$PC$_6$H$_{13}$); anions (α-sulfonyl, α-cyano, α-nitro and vinylogous analogs (⌐\Li\SO$_2$Ph, ⌐\Li\CN, ⌐\Li\NO$_2$)); Peterson olefination reagent; or enolate (aldehyde, ketone, lactone enolate, and vinylogous analogs (⌐\O\Li, Li⌐\O\O)))

D = organometallic reagent of lithium and magnesium; anions (α-sulfonyl, α-cyano, α-nitro and vinylogous analogs (⌐\Li\SO$_2$Ph, ⌐\Li\CN, ⌐\Li\NO$_2$)); or enolate (aldehyde, ketone, lactone enolate, and vinylogous analogs (⌐\O\Li, Li⌐\O\O)). More preferably: Wittig reagent (BrPh$_3$P~~~COOMe, BrPh$_3$P~~~COOMe, BrPh$_3$PC$_8$H$_{17}$COOH); or Petersons olefination reagent (organosilyl reagents).

R$_C$ = the organic moiety after coupling of C

R$_D$ = the organic moiety after coupling of D

*FIG. 3A*

$Z$ = O; S; $NR_2$ $R$ = alkyl (Me, Et, t-Bu, $ArCH_2$, i-Pr, $Ph_3C$, THP); aryl (Ph, $4-NO_2C_6H_4$, $4-MeOC_6H_4$); acyl ($CH_3-CO-$, $Ph-CO-$, $Ph-CO-CH_2$, $X_3C-CO-$); or silyl (trialkylSi, $t-BuPh_2Si$) group $R_1$ = alkyl (Me, Et, t-Bu, $ArCH_2$, i-Pr, $Ph_3C$, THP); acyl ($Ph-CO-$, Ac, pivaloate, $X_3C-CO-$); sulfonate (Ts, mesylate, triflate); or silyl (trialkylSi, $t-BuPh_2Si$) group $R_2$ = $R$ or $R_1$ $R_3$ = $(CH_2)_n-OR_1$ and n=1-10; carbonyl ($(CH_2)_n$ CHO and n=0-10); halides ($C_nH_{2n}X$ and X=Cl, Br, I, and n=1-10); alkyne ($C_nH_{2n-3}$ and n=2-10); alkene ($C_nH_{2n-1}$ and n=2-10); alkane ($C_nH_{2n+1}$ and n=1-10)

*FIG. 3B*

C = organometallic reagent of tin, lithium, cerium, cesium, copper (I), copper (II), titanium, magnesium, and silicon (BuLi, CuC$_5$H$_{11}$, CuLi (⌐\C$_5$H$_{11}$)$_2$, CuLiBu$_2$, CuLi(C$_5$H$_{11}$)$_2$, C$_5$H$_{11}$MgX, BuMgX); Wittig reagent (BrPh$_3$PC$_6$H$_{13}$); anions (α-sulfonyl, α-cyano, α-nitro and vinylogous analogs (∼∼SO$_2$Ph, ∼∼CN, ∼∼NO$_2$ with Li)); Peterson olefination reagent; or enolate (aldehyde, ketone, lactone enolate, and vinylogous analogs (∼∼C(O)-Li, Li-C(O)-O ring))

D = organometallic reagent of lithium and magnesium; anions (α-sulfonyl, α-cyano, α-nitro and vinylogous analogs (∼∼SO$_2$Ph, ∼∼CN, ∼∼NO$_2$ with Li)); or enolate (aldehyde, ketone, lactone enolate, and vinylogous analogs (∼∼C(O)-Li, Li-C(O)-O ring)). More preferably: Wittig reagent (BrPh$_3$P∼=∼COOMe, BrPh$_3$P∼=∼COOMe, BrPh$_3$PC$_8$H$_{17}$COOH); or Petersons olefination reagent (organosilyl regents).

R$_C$ = the organic moiety after coupling of C

R$_D$ = the organic moiety after coupling of D

FIG. 4A $Z = O; S; NR_2$ $R$ = alkyl (Me, Et, t-Bu, ArCH$_2$, i-Pr, Ph$_3$C, THP); aryl (Ph, 4-NO$_2$C$_6$H$_4$, 4-MeOC$_6$H$_4$); acyl (CH$_3$-CO-, Ph-CO-, Ph-CO-CH$_2$, X$_3$C-CO-); or silyl (trialkylSi, t-BuPh$_2$Si) group $R_1$ = alkyl (Me, Et, t-Bu, ArCH$_2$, i-Pr, Ph$_3$C, THP); acyl (Ph-CO-, Ac, pivaloate, X$_3$C-CO-); sulfonate (Ts, mesylate, triflate); or silyl (trialkylSi, t-BuPh$_2$Si) group $R_2$ = R or R$_1$ $R_3$ = (CH$_2$)$_n$-OR$_1$ and n=1-10; carbonyl ((CH$_2$)$_n$ CHO and n=0-10); halides (C$_n$H$_{2n}$X and X=Cl, Br, I, and n=1-10); alkyne (C$_n$H$_{2n-3}$ and n=2-10); alkene (C$_n$H$_{2n-1}$ and n=2-10); alkane (C$_n$H$_{2n+1}$ and n=1-10)

*FIG. 4B*

FUNCTIONALIZING CARBOHYDRATE DERIVATIVES BY BASE-INDUCED β-ELIMINATIOM FORMING BIOACTIVE DERIVATIVES CONTAINING HYDROXY-DIENE SUBUNITS

The U.S. Government may own certain rights in the present invention pursuant to USPHS NIH Grant Number GM 31278.

BACKGROUND OF THE INVENTION

The present invention relates to functionalizing carbohydrate derivatives by base-induced β-elimination and subsequent olefination to form products containing a subunit having at least one hydroxyl group and a diene group. More specifically, the present invention relates to functionalizing derivatives of 2-deoxyfuranoses and derivatives of 2-deoxypyranoses by base-induced β-elimination and subsequent olefination to form biologically active derivatives of fatty acids containing α-hydroxy-diene groups and α,β-dihydroxy-diene groups, respectively.

The oxidative metabolism of arachidonic acid yields a variety of biologically active substances which are thought to serve as mediators of intracellular events within tissue (Samuelsson, B., et al. (1978) Annu. Rev. Biochem. 42: 997; Lewis, R. A., et al. (1982) Int. J. Immunopharmacol. 4: 85). Action by the cyclooxygenase enzyme leads to the production of prostaglandins (Lands, W. E. M., et al. (1983) Prostaglandins and Related Substances (Pace-Asciak, C., and Granstrom, E., eds) pp. 203–222, Elsevier Scientific Publishing Co., Amsterdam), prostacyclin (Moncado, S., et al. (1987) Thromb. Res. 11: 323), and thromboxanes (Hamberg, M., et al. (1973) Proc. Natl. Acad. Sci. U.S.A. 70: 899), while action by the 5-lipoxygenase enzyme leads to the production of leukotriene $A_4$ which is the precursor for the sulfidopeptide leukotrienes (slow reacting substance of anaphylaxis) (Murphy, R. C., et al. (1979) Proc. Natl. Acad. Sci. U.S.A. 76: 4275) as well as the chemotactic factor for neutrophils, leukotriene $B_4$ (Borgeat, P., et al. (1979) J. Biol. Chem. 254: 7865). In addition, there are other lipoxygenases which catalyze the production of 12(S)-hydroxyeicosatetraenoic acid (Nugteren, D. H. (1975) Biochim. Biophys. Acta 380: 299) and 15(S)-hydroxyeicosatetraenoic acid (Narumiya, S., et al. (1981) J. Biol. Chem. 256: 9583). Arachidonic acid could also serve as a substrate for hepatic cytochrome P-450 in the generation of hydroxy and epoxy metabolites of this polyunsaturated fatty acid (Capdevila, J., et al. (1981) Proc. Natl. Acad. Sci. U.S.A. 78: 5362; Oliw, E. H., et al. (1982) J. Biol. Chem. 257: 3771; Morrison, A., et al. (1981) Proc. Natl. Acad. Sci. U.S.A. 78: 7375). These molecules, in particular the epoxyeicosatrienoic acids, have potent pharmacological actions releasing peptide hormones such as luteinizing hormone (Snyder, G. D., et al. (1983) Proc. Natl. Acad. Sci. U.S.A. 80: 3504), prolactin (Cashman, J. R., et al. (1987) Neuroendocrinology 46: 246), and somatostatin (Capdevila, J., et al. (1983) Endocrinology 113: 421) from brain tissue, as well as insulin from pancreatic islet cells (Falck, J. R., et al. (1983) Biochem. Biophys. Res. Commun. 114: 743). Furthermore, the cytochrome P-450-derived epoxides have significant effects on the inhibition of chloride transport (Jacobson, H. R., et al. (1984) Prostaglandins and Membrane Ion Transport (Braquet, P., et al. eds) pp. 311–318, Raven Press, New York), inhibition of platelet aggregation (Fitzpatrick, F. A., et al. (1986) J. Biol. Chem. 261: 15334), the ability to mobilize microsomal calcium ions (Kutsky, P., et al. (1983) Prostaglandins 26: 13), and have the property to inhibit calcium ionophore-induced neutrophil aggregation (Kraemer, R., et al. (1987) Am. J. Pathol. 128: 446). It was described that the 12(R)-hydroxyeicosatetraenoic acid (12(R)-HETE), produced by cytochrome P-450 from the bovine corneal epithelial cells, was a potent inhibitor of the $Na^+/K^+$-ATPase in the cornea (Schwartzman, M. L., et al. (1987) Proc. Natl. Acad. Sci. U.S.A. 84: 8125).

Recently, it was shown that when corneal microsomes were incubated with arachidonic acid in the presence of an NADPH-generating system, four metabolites were found. Two of these were biologically active; one of the metabolites, 12(R)-HETE, was found to inhibit partially purified $Na^+/K^+$-ATPase from the corneal epithelium in a dose-dependent manner with an $ID_{50}$ of 50 nM. The second compound, 12(R)-hydroxy-5,8,14-eicosatrienoic acid, was found also to be biologically active, leading to vascular reactivity and vasodilation in the intact eye (Schwartzman, M. L., et al. (1987) Invest. Opthalmol. Visual Sci. 3: Suppl. 28, 328). The latter compound is the vasodilator (Murphy, R. C., et al. (1988) J. Biol. Chem. 263: 17197).

U.S. Pat. No. 4,906,467 to Schwartzman, et al. discloses the use of salts or esters of 12(R)-HETE to reduce intraocular pressure in a patient. The compound was found to be particularly useful in treatment of all types of glaucoma. Administering 12(R)-HETE to a patient also is useful in lowering intraocular pressure in preparation for eye surgery, particularly for the removal of cataracts. One of the primary advantages of this compound is that it is normally found in the eye, so side effects of the compound are minimal. Schwartzman, et al. also discloses that the compound 12(R)-HETE causes a decrease in intraocular pressure for a period of several days.

Psoriasis is associated with enhanced synthesis of 12-HETE (Woollard, P. M. (1986) Biochem. Biophys. Res. Commun. 136: 169). 12-HETE is also the major lipoxygenase product of platelets (Hamberg, M. and Samuelsson, B. (1980) Biochem. Biophys. Res. Commun. 95: 1090). Woollard, however, demonstrated that whereas the platelet enzyme produces the 12(S) isomer, that formed by the psoriatic lesions was 12(R)-HETE. This difference in stereochemical configuration endows the 12-HETE with quantitatively different activities.

The compound 12(R)-HETE has been shown to possess potent human neutrophil chemotactic and chemokinetic properties (Dowd, P. M., et al., (1987) J. Invest. Dermatol. 88: 120). The 12(S) isomer is much less potent (Cunningham, F. M. and Woollard P. M. (1987) Prostaglandins 34: 71).

The 5- and 15-lipoxygenase products, leukotriene $B_4$ (LTB4) and 15-hydroxyeicosatetraenoic acid (15-HETE), respectively, have been described in keratome specimens of psoriatic skin lesions (Fogh, K., et al., (1987) Arch. Dermatol. Res. 279: 504), and in exudates from abraded psoriatic plaques (Barr, R. M., et al. (1984) Prostaglandins 28: 57. See also, Baer, A. N., et al. (1990) J. Lipid Res. 31: 125).

In view of the diverse biological activities of the metabolic compounds of arachidonic acids, sufficient amounts of enantiomerically pure compounds are needed for their pre-clinical or clinical uses and for their further biological evaluations. Most of those metabolites of arachidonic acids contain α-hydroxy-diene subunits or α,β-dihydroxy-diene subunits.

Isolation of these active metabolites from biological sources is tedious and seldom gives enough quantities for the necessary uses and studies.

Chemical synthesis is an alternate way to obtain enantiomerically pure metabolites of arachidonic acids in larger quantities. Chemical syntheses of 13-hydroxy-9Z, 11E-octadecadienoic acid (13-HODE), and 12-HETE have been reported: Leblanc, Y., et al. (1986) *J. Org. Chem.* 51: 789, and cited references; Fretland, D. J. and Djuric, S. W. (1989) *Leuk. Essent. Fatty Acids* 38: 215, and cited references; De Montarby, L., et al. (1989) *Bull Soc. Chim. Fr.* 419, and cited references; Just, G. and Wang, Z. Y. (1985) *Tetrahedron Lett.* 26: 2993; Rao, A. V. R., et al. (1985) *Tetrahedron Lett.* 26: 465; Chan, C., et al. (1988) *J. Chem. Soc., Chem. Commun.* 971; Nicolaou, K. C. and Abe, R. Y. (1989) *Synthesis* 898; Taffer, I. M. and Zipkin, R. E. (1987) *Tetrahedron Lett.* 28: 6543; Corey, E. J., et al. (1978) *J. Am. Chem. Soc.* 100: 1942; Just, G. and Wang, Z. Y. (1986) *J. Org. Chem.* 51: 4796; Yadagiri, P., et al. (1986) *Tetrahedron Lett.* 27: 6039; Mosset, P., et al. (1986) *Tetrahedron Lett.* 27: 6035; Moustakis, C. A., et al. (1986) *Tetrahedron Lett.* 27: 303; Corey, E. J., et al. (1980) *J. Am. Chem. Soc.* 102: 1433; and Djuric, S. W., et al. (1988) *Tetrahedron Lett.* 29: 3459.

Unfortunately, the reported syntheses for these biologically active metabolites involve multiple synthetic steps. Almost invariably, the total yield from each of these reported syntheses is extremely low. Therefore, there is an urgent need for simple, versatile, concise, and convergent stereocontrolled chemical syntheses of these compounds.

SUMMARY

It is thus advantageous, and this is one of the objects of this invention, to provide a unique method for functionalizing a carbohydrate derivative, or its analog, by base-induced β-elimination and subsequent olefination to produce a desired compound containing an α-hydroxy-diene subunit or an α,β-dihydroxy-diene subunit, thus providing a versatile and concise synthesis of the desired compound having biological activities.

One aspect of the present invention relates to a process for functionalizing a substituted and protected carbohydrate derivative. The process involves the steps of: (1) Coupling a first substituted and protected carbohydrate derivative with a first coupling reagent to yield a second substituted and protected carbohydrate derivative; (2) deprotecting the second substituted and protected carbohydrate derivative to yield a substituted and deprotected carbohydrate derivative, which is characterized as having a free hydroxyl group at its C-1 position; (3) coupling the substituted and deprotected carbohydrate derivative with a second coupling reagent; and thereby effecting an base-induced β-elimination and subsequent olefination to form a compound containing a subunit having at least one hydroxyl group and a diene group, such as an α-hydroxy-diene subunit or an α,β-dihydroxy-diene subunit.

Among other advantages, the functionalization in this invention creates, in "one pot," a compound having three functional groups: (1) an α-hydroxyl group or an α,β-dihydroxyl group, depending on the starting material; (2) an E double bond formed by β-elimination; and (3) another E or Z double bond formed by a coupling reagent, such as a Wittig reagent.

Furthermore, the stereo-configuration of the hydroxy-diene subunit is easily controlled by the selection of a suitable starting material and the reaction conditions.

Also, it is an advantage to obtain a desired hydroxyl group in the final compound without any unnecessary manipulating steps.

Ordinarily, a free hydroxyl group in a chemical compound is extremely labile, that is, this hydroxyl group cannot survive many of the reaction conditions. Thus, customarily, a free hydroxyl group must first be protected prior to undergoing other reaction steps, and the protected hydroxyl group must then be liberated by deprotection at the end of the reaction steps. This protection and deprotection of hydroxyl group not only means two additional manipulative steps, but also lowers the overall reaction yield.

In contrast, the "protection" and the "deprotection" of the desired α-hydroxyl or β-hydroxyl group in the present invention is carried out inherently in the functionalization. In the present invention, the desired α-hydroxyl or β-hydroxyl group is inherently "protected" by the ring structure of the starting material; and the desired hydroxyl group is inherently "released" when the ring is opened through a final coupling olefination. Thus, the functionalization as described in the present invention eliminates the necessity of formally protecting and deprotecting a hydroxyl group. If necessary, this hydroxyl group can be, for example: (1) Inverted to its stereoisomer (using diethylazodi-carboxylate (DEAD), triphenyl phosphine and benzoic acid); (2) converted to a sulfur derivative (using a sulfur nucleophile such as DEAD, triphenyl phosphine and thioacetic acid); and (3) converted to a hydroperoxy group (using mesyl chloride, then hydrogen peroxide). Further, a derivative of the α, β-dihydroxyl group can be converted to an epoxide (using a base, such as sodium methoxide).

The present invention also provides a facile, convenient and general functionalizing method which can be used for the synthesis of derivatives of fatty acids containing α-hydroxy-diene subunits or α, β-dihydroxy-diene subunits through functionalization of substituted 2-deoxyfuranoses, their respective analogs, or substituted 2-deoxypyranoses, and their respective analogs. Examples of such fatty acid derivatives are biologically active metabolites of arachidonic and related acids.

This invention also relates to a process for the preparation of a derivative of fatty acid containing an α-hydroxy-diene or an α, β-dihydroxy-diene subunit, depending on the starting material. The process involves the steps of: (1) Coupling a first substituted and protected carbohydrate derivative with a first coupling reagent, such as an organometallic reagent, to yield a second substituted and protected carbohydrate derivative; (2) deprotecting the second substituted and protected carbohydrate derivative to yield a substituted and deprotected carbohydrate derivative, this substituted and deprotected carbohydrate derivative is characterized as having a free hydroxyl group at its C-1 position; and (3) coupling the substituted and deprotected carbohydrate derivative with a second coupling reagent, such as a Wittig reagent, and thereby effecting a base-induced β-elimination and subsequent olefination to form the derivative of fatty acid containing an α-hydroxy-diene or an α, β-dihydroxy-diene subunit. If needed, the derivative formed can be further subjected to hydrolysis to yield the corresponding free acid. Likewise, the hydroxyl group or groups can be further converted to other functional group or groups. Alternatively, the process involves the steps of: (1) Coupling a starting material, a first substituted carbohydrate derivative unprotected at C-1 position, i.e. having a free hydroxyl group at the C-1 position, with a first coupling reagent, such as a Wittig reagent, to yield an unprotected product containing an α-hydroxy-diene or an α, β-dihydroxy-diene subunit, depending upon the starting material; (2) protecting the hydroxyl group generated in the unprotected product to give a protected product; (3) coupling the protected product with a second coupling reagent, such as an organometallic reagent, to give a precursor of a fatty acid derivative containing a protected α-hydroxy-diene or a protected α, β-dihydroxy-diene subunit, depending upon the starting material; and (4) deprotecting the precursor to give the fatty acid derivative containing an α-hydroxy-diene or an α, β-dihydroxy-diene subunit, depending upon the starting material.

BRIEF DESCRIPTION OF THE FIGURES

FIGS. 1A and 1B depict different possible substitutions for compounds appearing in the scheme shown in FIG. 1;

FIGS. 2A and 2B depict different possible substitutions for compounds appearing in FIG. 2;

FIGS. 3A and 3B depict different possible substitutions for the compounds appearing in the scheme shown in FIG. 3;

FIGS. 4A and 4B depict different possible substitutions for the compounds appearing in the scheme shown in FIG. 4;

DETAILED DESCRIPTION OF THE INVENTION

The abbreviations used herein are: HETE, hydroxyeicosatetraenoic acid; LTB$_4$, leukotriene B$_4$, 5(S), 12(R)-dihydroxyeicosa-(6Z, 8E, 10E, 14Z)-tetraenoic acid; HODE, hydroxyoctadecadienoic acid; HEPE, hydroxyeicosapentaenoic acid, DiHETE, dihydroxyeicosatetraenoic acid; Lipoxin A$_4$, 5(S), 6(R), 15(S)-trihydroxyeicosa-(7E, 9E, 11Z, 13Z)-tetraenoic acid; and Leukotriene A$_3$, 5(S), 6(S)-epoxyeicosa-(7E, 9E, 11Z)-trienoic acid.

Broadly, the functionalization of the present invention can be represented by the reaction schemes represented in FIG. 1 through FIG. 4.

Figure 1:
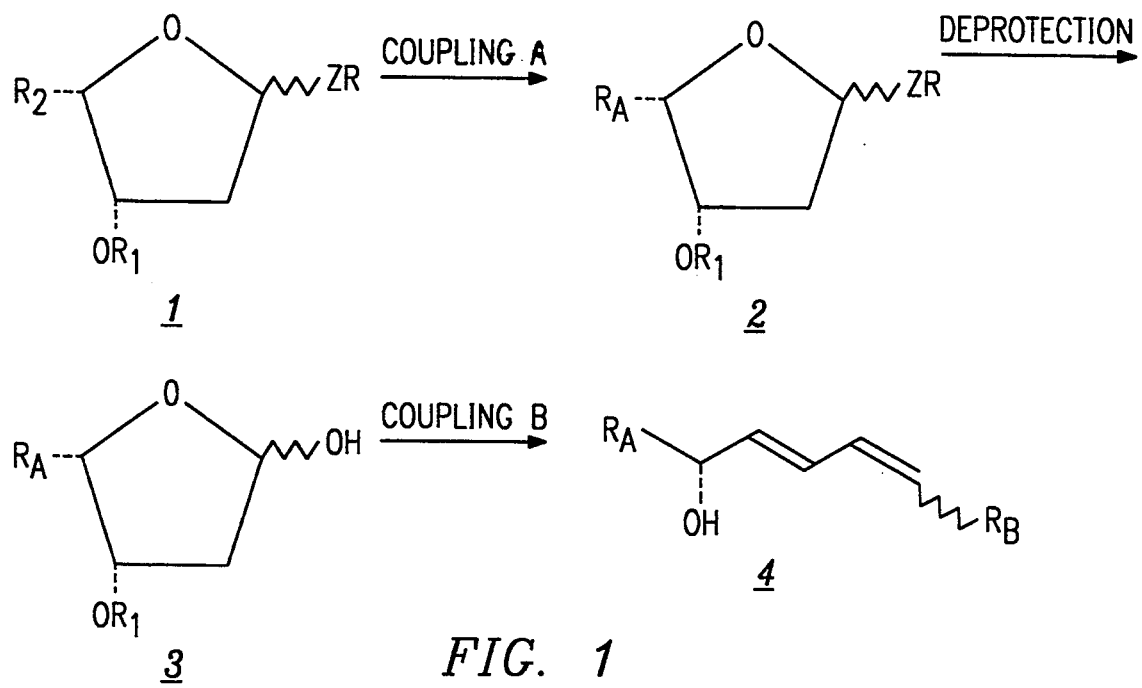
FIG. 1 shows a scheme for the functionalization of substituted 2-deoxyfuranoses or their analogs to form derivatives of α-hydroxy-diene fatty acid.

In FIG. 1, substituted and protected 2-deoxyfuranose 1 is reacted with a first coupling reagent A. The reaction product 2, having a ZR functional group at the C-1 position, is then deprotected and hydrolyzed to give a substituted and deprotected compound 3 having a free hydroxyl group at the C-1 position. Finally, the substituted and deprotected compound 3 is reacted with a second coupling reagent B thereby effecting an base-induced β-elimination and subsequent olefination to form an α-hydroxy-diene fatty acid derivative 4. The free α-hydroxyl group shown in compound 4 is derived from the ring oxygen of compound 1. The squiggle line as used denotes a mixture of possible stereoisomers, such as anomers, having a mixture of both "up" and "down" stereo-configurations; while the dashed line denotes a pure stereoisomer having either an "up" or a "down" stereo-configuration. Preferably, R$_2$ is a "coupling" group, while R$_1$ is an "eliminating" group. Different possible substitutions for compounds appearing in FIG. 1 are shown in FIGS. 1A and 1B. R$_A$ and R$_B$ denote the organic moiety after coupling of A and B, respectively. Thus, for a derivative of 2-deoxy-D-ribofuranose, such as 19 in FIG. 5:

if A is CuLiBu$_2$, R$_A$ is C$_5$H$_{11}$, if B is BrPh$_3$P(CH$_2$)$_8$COOH, R$_B$ is (CH$_2$)$_7$COOH;

and if A is CuLi(C$_5$H$_{11}$)$_2$, R$_A$ is C$_5$H$_{11}$, if B is BrPh$_3$PCOOMe, R$_B$ is COOMe.

Figure 2:
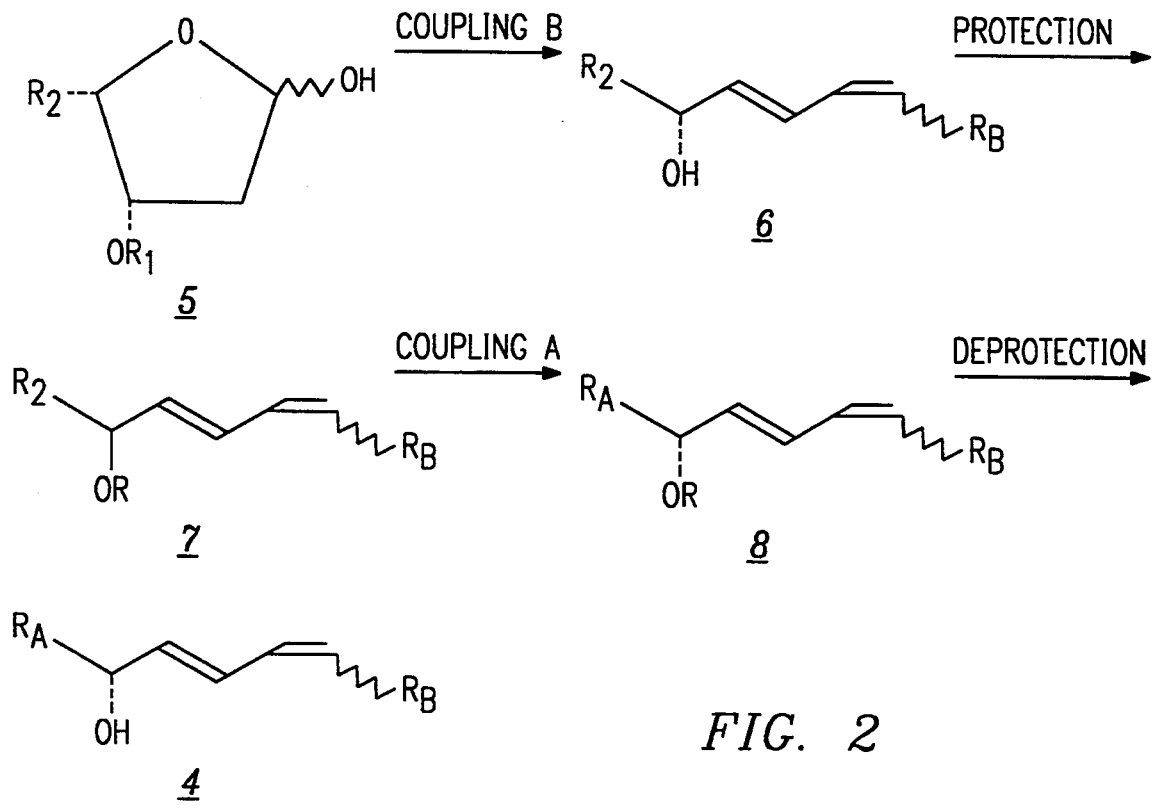
FIG. 2 shows an alternative scheme for the functionalization of substituted 2-deoxyfuranoses or their analogs to form derivatives of fatty acid having α-hydroxy-diene subunits.

FIG. 2 shows an alternative scheme for functionalizing a 2-deoxyfuranose derivative to give a derivative of fatty acid containing an α-hydroxy-diene subunit. Substituted and deprotected 2-deoxyfuranose 5, having a free hydroxyl group at the C-1 position, is reacted with a first coupling reagent B to yield an unprotected product, 6, containing an α-hydroxy-diene subunit. Protection of the α-hydroxyl group in 6 yields a protected product, 7, which can be then reacted with a second coupling reagent A to give a precursor, 8, of a fatty acid derivative containing a protected α-hydroxy-diene subunit. Deprotection of precursor 8 yields 4, a fatty acid derivative containing an α-hydroxy-diene subunit. Preferably, R$_2$ is a "coupling" group, while R$_1$ is an "eliminating" group. The squiggle line as used denotes a mixture of possible stereoisomers, such as anomers, having a mixture of both "up" and "down" stereo-configurations. The dashed line denotes a pure isomer having either an "up" or a "down" stereo-configuration. Different possible substitutions for compounds appearing in FIG. 2 are shown in FIGS. 2A and 2B.

Thus, the base-induced β-elimination and the subsequent olefination as shown in both FIG. 1 and FIG. 2 create, in "one pot," a compound having three functional groups: (1) An α-hydroxyl group; (2) an E double bond formed by β-elimination; and (3) another E or Z double bond formed by a coupling reaction. As a result of this functionalization, a biologically active compound can be formed. For ease of separation and handling, the carboxylic groups of the fatty acid derivatives may be generated in ester forms, which, upon standard hydrolysis, will readily afford the corresponding free acids.

Figure 3:
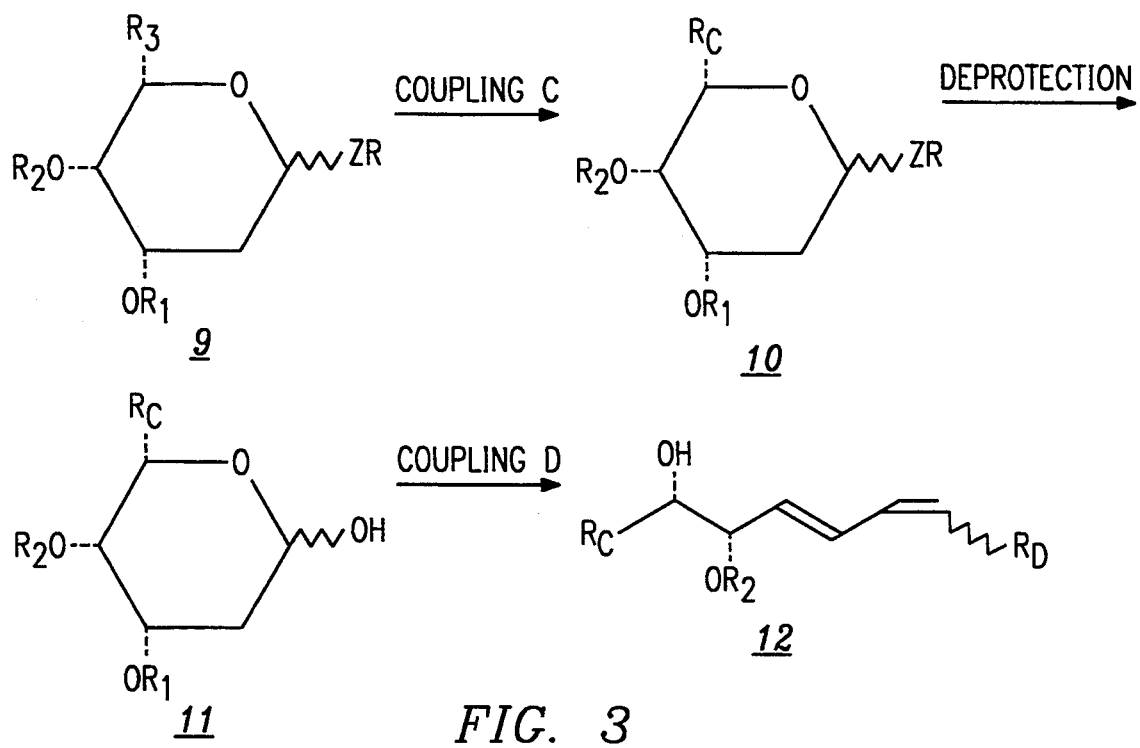
FIG. 3 shows a scheme for the functionalization of substituted 2-deoxypyranoses or their analogs to form derivatives of fatty acid having α, β-dihydroxy-diene subunits.

In FIG. 3, substituted and protected 2-deoxypyranose 9 is reacted with a first coupling reagent C to give 10. The reaction product 10, having a ZR functional group at the C-1 position, is then deprotected and hydrolyzed to give a substituted and deprotected compound 11 having a free hydroxyl group at the C-1 position. Finally, the substituted and deprotected compound 11 is reacted with a second coupling reagent D thereby effecting a base-induced β-elimination and subsequent olefination to form a α, β-dihydroxy-diene fatty acid derivative 12. The free β-hydroxyl group shown in compound 12 is derived from the ring oxygen of compound 9. The $R_2$ group in 12 can be easily removed by standard hydrolysis. Again, the squiggle line here denotes a mixture of possible stereoisomers, such as anomers, having a mixture of both "up" and "down" stereoconfigurations; while the dashed line denotes a pure isomer having either an "up" or a "down" stereo-configuration. Preferably, $R_3$ is a "coupling" group and $R_1$ is an "eliminating" group. Different possible substitutions for compounds appearing in FIG. 3 are shown in FIGS. 3A and 3B. $R_C$ and $R_D$ denote the organic moiety after coupling of C and D, respectively. Thus, for derivatives of 2-deoxy-D-galactopyranose, such as 39 in FIG. 8:

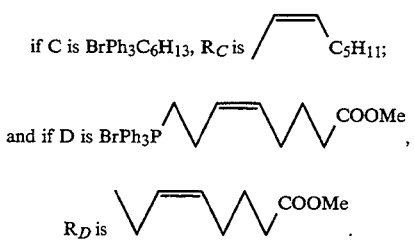

Figure 4:
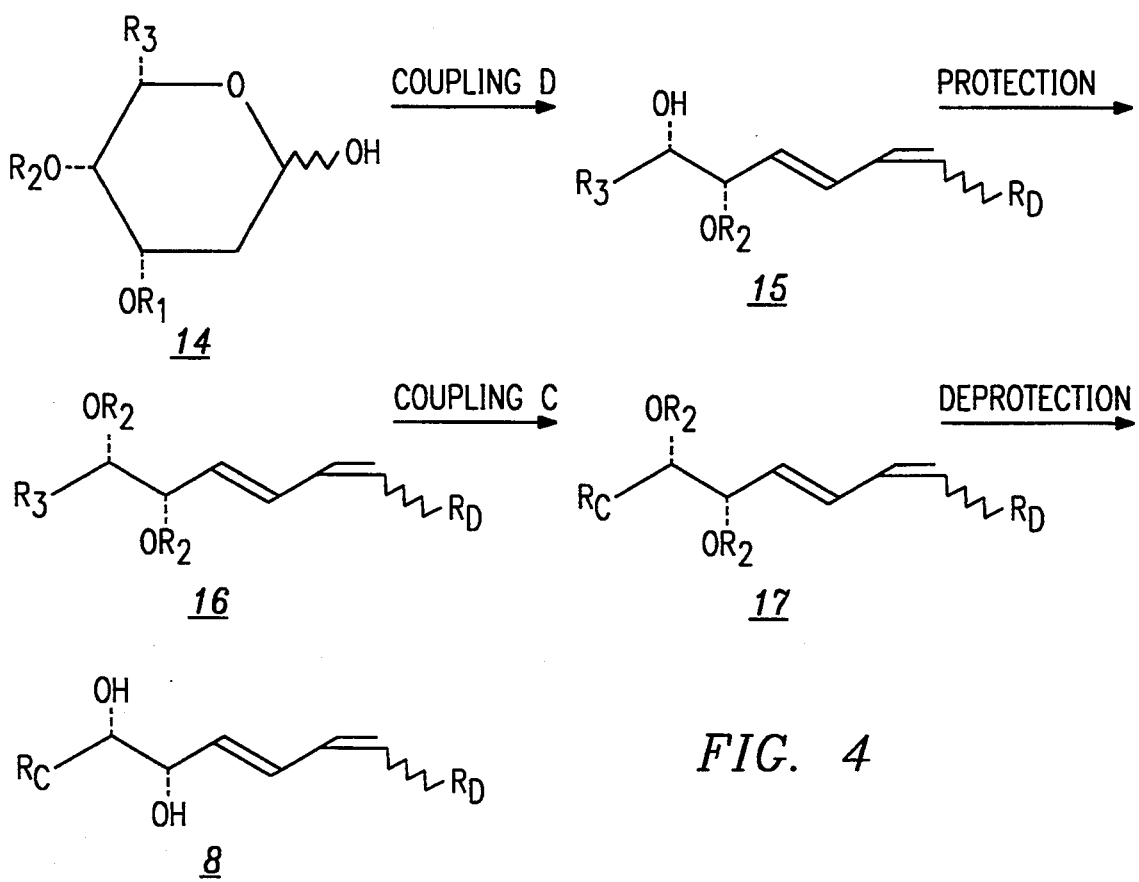
FIG. 4 shows an alternative scheme for the functionalization of substituted 2-deoxypyranoses or their analogs to form derivatives of fatty acid having α, β-dihydroxy-diene subunits.

FIG. 4 depicts an alternative scheme for functionalizing a derivative of 2-deoxypyranose to give a derivative of fatty acid containing an α, β-dihydroxy-diene subunit. Substituted and deprotected 2-deoxypyranose; 14, having a free hydroxyl group at the C-1 position, is reacted with a first coupling reagent D to give an unprotected product, 15, containing an α, β-dihydroxy-diene subunit. Protection of the free β-hydroxyl group of 15 yields 16, which can then be reacted with a second coupling reagent C to give a precursor, 17, of a fatty acid derivative containing an α, β-dihydroxy-diene subunit. For ease of subsequent deprotection, an $R_2$ group is selected to protect the free β-hydroxyl group. Deprotection of precursor 17 yields 8, a fatty acid derivative containing an α, β-dihydroxy-diene subunit. The squiggle line denotes a mixture of possible stereoisomers, such as anomers, having a mixture of both "up" and "down" stereo-configurations. The dashed line denotes a pure isomer having either an "up" or a "down" stereo-configuration. Different possible substitutions for compounds appearing in FIG. 4 are shown in FIGS. 4A and 4B. Preferably, $R_3$ is a "coupling" group and $R_1$ is an "eliminating" group.

Thus, the base-induced β-elimination and subsequent olefination as shown in both FIGS. 3 and 4 create, in "one pot," a compound having three functional groups: (1) An α, β-dihydroxyl group; (2) an E double bond formed by β-elimination; and (3) another E or Z double bond formed by a coupling reaction. As a result of this functionalization, a biologically active compound can be prepared. For ease of separation and handling, the carboxylic groups of the fatty acid derivatives may be generated in ester forms, which, upon standard hydrolysis, will readily afford the corresponding free acids. Another advantage of the present invention is the inherent "selective" protection of the two hydroxyl groups, α and β, in compounds 12 and 15. Such selective protection affords an opportunity to convert and manipulate the two hydroxyl groups into other different and separate functional subunits.

The following examples are intended to illustrate the invention and are not to be construed as being limitations thereon.

Tetrahydrofuran (THF) was distilled from sodium/-benzophenone immediately prior to use. Diethyl ether ($Et_2O$), toluene dichloromethane ($CH_2Cl_2$) and hexamethylphosphoramide (HMPA) were distilled from $CaH_2$ (HMPA at reduced pressure) and stored under a nitrogen atmosphere. All other solvents were of reagent grade from freshly opened bottles. All reactions were carried out under an inert atmosphere of nitrogen or argon and were monitored by thin-layer chromatography (TLC). TLC and column chromatography were carried out in silica gel.

Figure 5:
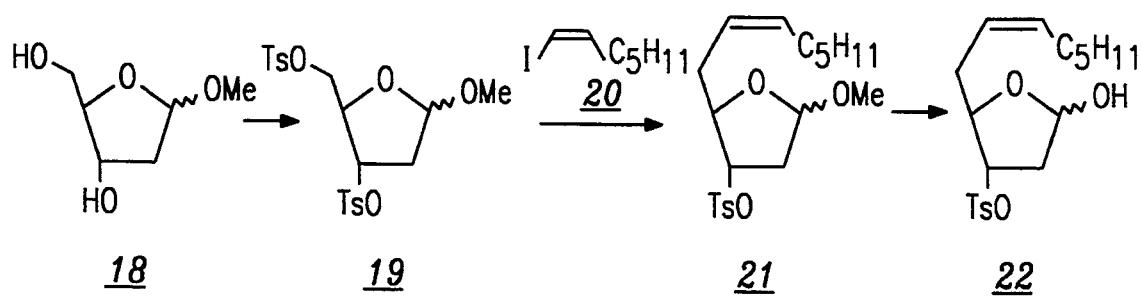
FIG. 5 shows a scheme for the functionalization of a bistosyl compound to form 12(R)-HETE.
Figure 5:
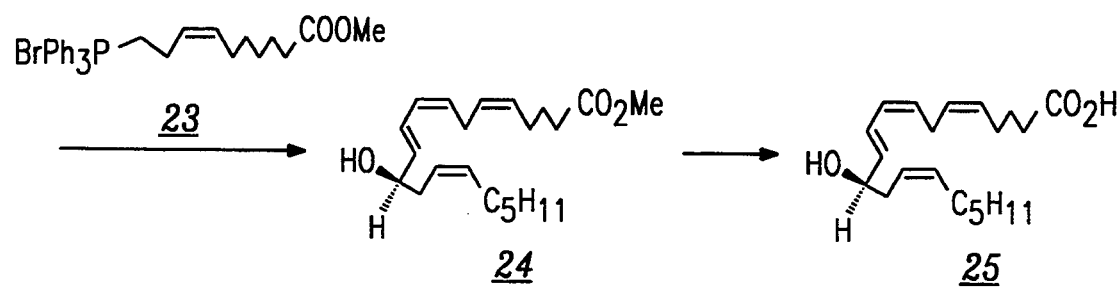

Briefly, FIG. 5 shows a reaction scheme in which methyl furanoside, or diol, 18, obtained as an anomeric mixture from commercial 2-deoxy-D-ribose in high yield, was readily converted to a novel lactol 21 via selective coupling of the bis-tosylate 19 with the higher order cuprate generated from (Z)-1-iodo-1-heptene, 20, in diethyl ether and subsequent mild acid hydrolysis. Creation of the E,Z-diene exploited a facile, ylide-induced elimination of tosylate from the open-chain tautomer of 22 under the conditions utilized for Wittig olefination. In situ condensation of the resultant E-enal with 7-carbomethoxyhepta-3(Z)-en-1-ylidene-triphenylphosphorane, furnished 12(R)-HETE methyl ester 24. Hydrolysis of 24 afforded the corresponding free acid 25. FIG. 5 shows the following examples:

EXAMPLE 1

The diol, 18, (1 g) was dissolved in a mixture of 100 ml of pyridine:dichloromethane (4:6) and the mixture solution was cooled to 0° C. Tosyl chloride (4 equiv.) was added into the solution and the resulting mixture was stirred at 0° C. for 12 hours. The reaction mixture was then diluted with dichloromethane (100 ml), washed with saturated aqueous $CuSO_4$ (3×100 ml), water and brine successively. The organic phase was dried over anhydrous sodium sulfate, filtered, then the filtrate was concentrated at reduced pressure. Chromatography of the residue with 20%–50% ethyl acetate in hexane yielded a new bis-tosylate, 19, (2.9 g), in 92% yield.

$R_f$=0.46 in 2% methanol in dichloromethane.

EXAMPLE 2

The (Z)-1-iodo-1-heptene, 20, (1.92 g, 10 equiv.) was dissolved in 20 ml ether and the mixture solution was cooled to −40° C. Then 5.4 ml of n-BuLi (1.6M) was added dropwise with stirring at about −40° C. to the mixture solution. Afterward, the mixture was stirred for 30 minutes at −40° C. Previously dried CuCN (385 mg, 5 equiv.) was added, and the reaction mixture was warmed to 0° C. in 30 minutes to form a pale-green solution. The solution was cooled to −40° C. again and a solution of the bistosylate, 19, (400 mg, $8.5 \times 10^{-4}$ mole) in a minimal amount of ether was added. The reaction mixture was stirred for 30 minutes at −40° C., then warmed to 0° C., and stirred at 0° C. for 4 hours. Workup with saturated aqueous $NH_4Cl$. The resulting mixture was extracted with ethyl acetate (3×50 ml). The combined organic extracts were dried over anhydrous sodium sulfate and filtered. The solvent was removed at reduced pressure. Chromatography of the residue with 10% ethyl acetate in hexane gave the desired product, 21, (217 mg) in 66% yield.

$R_f$=0.47 in ethyl acetate:hexane (1:2).

EXAMPLE 3

The ether compound, 21, (94 mg) was dissolved in an 8 ml mixture solution of acetic acid:THF:water (2:1:1). The solution was stirred at 70° C. for 8 hours. The reaction mixture was then diluted with excess toluene and the solvents were removed at reduced pressure. The residue was separated by TLC with a mixture of ethyl acetate:hexane (1:2) to give the desired product, 22, (47 mg), and unreacted starting material (29 mg). Yield of the product was 76% based on the recovered starting material.

$R_f$=0.35 in ethyl acetate:hexane (1:2).

EXAMPLE 4

The 7-carbomethoxyhepta-3(Z)-en-triphenylphosphonium bromide, 23, (210 mg, 3.5 equiv.) was dissolved in 3 ml of THF containing 300 μl of HMPA. The mixture was cooled to −20° C. Then 400 μl of $(Me_3Si)_2$ NNa (1M) was added dropwise and the reaction solution was stirred for 30 minutes at that temperature. Afterward, a solution of 40 mg of the lactol, 22, (0.1 mmol) in a minimal amount of THF was added and the reaction mixture was stirred at −20° C. for 1 hour. Workup with saturated aqueous $NH_4Cl$. The resulting mixture was extracted with ethyl acetate. The combined organic extracts were dried over anhydrous sodium sulfate and filtered. The solvent was then removed at reduced pressure. Chromatography of the residue with 10% ethyl acetate in hexane gave the product, 24, 27 mg in 78% yield.

$R_f$=0.46 in ethyl acetate:hexane (1:2).

Saponification with LiOH, MeOH, at 24° C. for 4 hours and then treated with HCl afforded the corresponding free acid 25.

Figure 6:
FIG. 6 shows a scheme for the functionalization of a bistosyl compound to form 13(R)-HODE.
Figure 6:
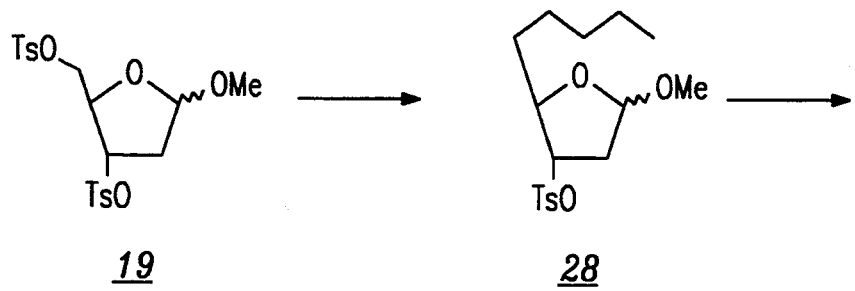
Figure 6:
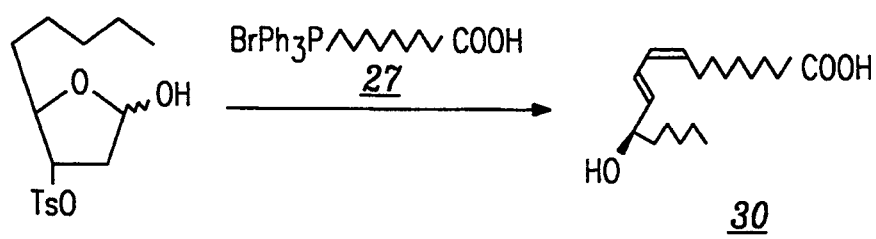

FIG. 6 shows that the extension of the general theme discussed above to 13(R)-HODE, 30, required homologation of 19 with dibutyl copper lithium in diethyl ether. Successive methyl lactol hydrolysis, generation of the corresponding E-enal and in situ olefination using 8-carboxyoctylidenetriphenylphosphorane smoothly provided 30. FIG. 6 shows the following examples:

EXAMPLE 5

The bromide, 26, (500 mg, 2.1 mmol) and the triphenylphosphine (1.1 g, 2 equiv.) were dissolved in 10 ml of acetonitrile. The mixture solution was stirred at 90° C. for 2 days. The solvent was removed at reduced pressure. Chromatography of the residue with dichloromethane progressingly increasing to 5%–10% methanol/dichloromethane yielded the salt, 27, (950 mg) in 90% yield.

$R_f$=0.23 in 10% methanol in dichloromethane.

EXAMPLE 6

To a suspension of 100 mg of CuI (5 equiv.) in 2 ml of ether, 0.66 ml of n-BuLi (1.6M, 10 equiv.) was added at −40° C., and the reaction mixture was stirred for 20 minutes to form a red-brown solution. A solution of the bis-tosylate, 19, (50 mg, 0.1 mmol) in a minimal amount of ether was added to the reaction mixture. The mixture was stirred at −40° C. for 3 hours. Workup with saturated aqueous $NH_4Cl$. The resulting mixture was extracted with ethyl acetate. The combined organic extracts were dried over anhydrous sodium sulfate and filtered. The solvent was removed at reduced pressure. Chromatography of the residue with 10% ethyl acetate in hexane gave the product, 28, (26 mg) in 75% yield.

$R_f$=0.47 in ethyl acetate:hexane (1:2).

EXAMPLE 7

The ether compound, 28, (26 mg) was dissolved in a 3 ml mixture solution of acetic acid:THF:water (1:1:1). The resulting solution was stirred at 70° C. for 12 hours. The reaction mixture was diluted with excess toluene and the solvents were removed at reduced pressure. The residue was separated by TLC with ethyl acetate:hexane (1:2) to give the produce, 29, (20 mg) in 80% yield.

$R_f$=0.22 in ethyl acetate:hexane (1:2).

EXAMPLE 8

The 8-carboxyoctyltriphenylphosphonium bromide, 27, (126 mg, 4 equiv.) was added to 4 ml of THF containing 400 ml of HMPA and the mixture was cooled to 0° C. Afterward, 430 μl of $(Me_3Si)_2NNa$ (1M) was added and the reaction mixture was stirred for 40 minutes at 0° C. to form orange solution. The solution was then cooled to −20° C. A solution of the lactol, 29, (18 mg) in a minimal amount of THF was added and the mixture was stirred for 30 minutes at −20 C. Workup with saturated aqueous $NH_4Cl$. The resulting mixture was extracted with ethyl acetate. The combined organic extracts were dried over anhydrous sodium sulfate and filtered. The solvent was then removed at reduced pressure. Chromatography of the residue with 20% ethyl acetate in hexane yielded the product, 30, (13 mg), in 86% yield.

$R_f$=0.18 in ethyl acetate:hexane (1:1).

Figure 7:
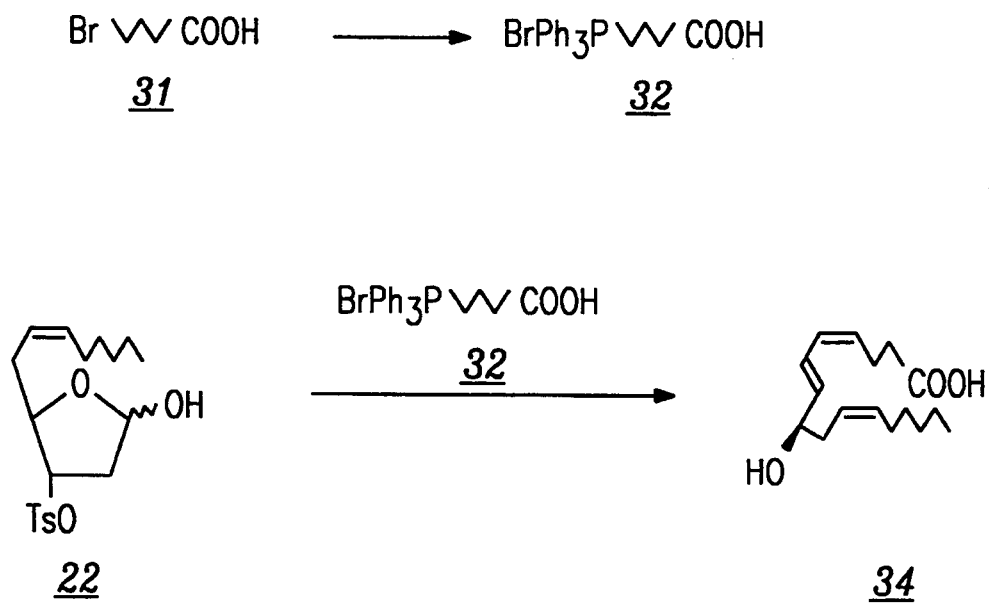
FIG. 7 shows a scheme for the functionalization of a lactol to form 8(R)-hydroxyhexadeca-4(Z), 6(E), 10(Z)-trienoic acid.

Briefly, FIG. 7 shows that analogous treatment of lactol 22 with 3-carboxypropyltriphenylphosphonium bromide, 32, yielded 8(R)-hydroxyhexadeca-4(Z), 6(E), 10(Z)-trienoic acid, 34, as a colorless oil. FIG. 7 shows the following examples:

EXAMPLE 9

The bromide, 31, (270 mg, 1.6 mmol) and the triphenylphosphine (2 equiv.) were dissolved in 10 ml of acetonitrile. The mixture solution was stirred at 70° C. for 2 days. The solvent was removed at reduced pressure. Chromatography of the residue with dichloromethane progressingly up to 5% methanol in dichloromethane gave the salt, 32, (450 mg), in 66% yield.

$R_f$=0.13 in 10% methanol in dichloromethane.

EXAMPLE 10

To a suspension of the 3-carboxypropyltriphenylphosphonium bromide, 32, (170 mg) in 4 ml of THF, was added 700 μl of (Me$_3$Si)$_2$NNa (1M) at 0° C. The reaction mixture was stirred for 30 minutes at 0° C. to form orange solution. The solution was cooled to −20° C. and a solution of the lactol, 22, (10 mg) in a minimal amount of THF was added. The reaction mixture was stirred at −20° C. for 30 minutes. After workup with saturated aqueous NH$_4$Cl, the resulting mixture was extracted with ethyl acetate. The combined organic extracts were dried and the solvent was removed at reduced pressure. Chromatography of the residue with 20% of ethyl acetate in hexane gave the product, 34, (2 mg).

EXAMPLE 11

Figure 8:
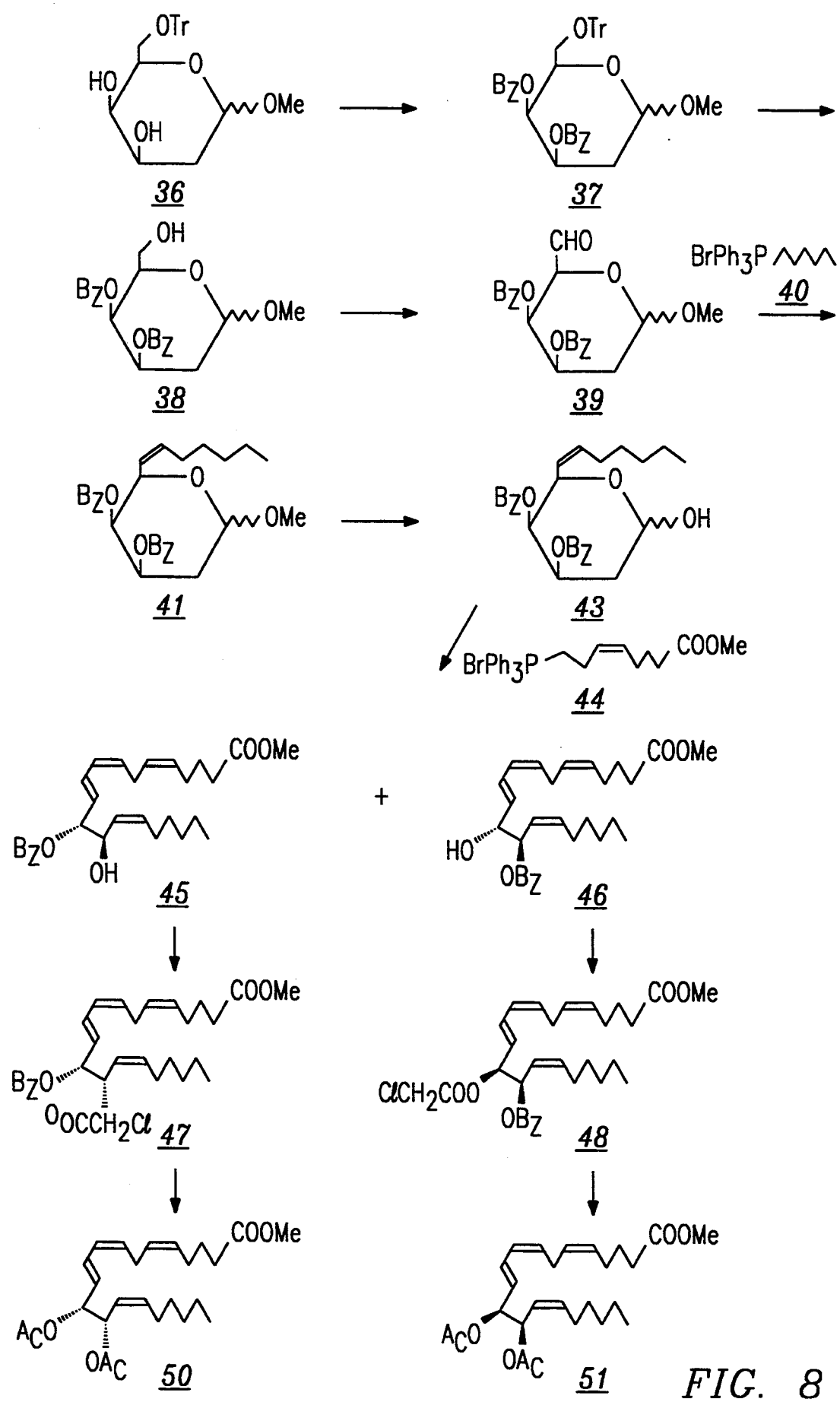
FIG. 8 shows a scheme for the functionalizing of a substituted 2-deoxy-D-galactopyranose to form derivatives of fatty acid containing α, β-diacetylated-diene subunits.

Compounds which can be formed in a manner analogous to the procedures described in the previous examples using appropriate starting materials:
(1) 12(R)-HETE
(2) 12(S)-HETE
(3) 5(R)-HETE
(4) 5(S)-HETE
(5) 8(R)-HETE
(6) 8(S)-HETE
(7) 9(R)-HETE
(8) 9(S)-HETE
(9) 11(R)-HETE
(10) 11(S)-HETE
(11) 15(R)-HETE
(12) 15(S)-HETE
(13) tetranor-12(R)-HETE
(14) tetranor-12(S)-HETE
(15) 5(R), 12(R)-DiHETE
(16) 5(S), 12(S)-DiHETE
(17) 5(R), 12(S)-DiHETE
(18) 5(S), 12(R)-DiHETE
(19) 5(R), 15(R)-DiHETE
(20) 5(S), 15(S)-DiHETE
(21) 5(R), 15(S)-DiHETE
(22) 5(S), 15(R)-DiHETE
(23) 8(R), 15(R)-DiHETE
(24) 8(S), 15(S)-DiHETE
(25) 8(R), 15(S)-DiHETE
(26) 8(S), 15(R)-DiHETE
(27) 12(R), 20-DiHETE
(28) 12(S), 20-DiHETE
(29) 5(R)-HEPE
(30) 5(S)-HEPE
(31) 8(R)-HEPE
(32) 8(S)-HEPE
(33) 9(R)-HEPE
(34) 9(S)-HEPE
(35) 11(R)-HEPE
(36) 11(S)-HEPE
(37) 12(R)-HEPE
(38) 12(S)-HEPE
(39) 15(R)-HEPE
(40) 15(S)-HEPE
(41) 9(R)-HODE
(42) 9(S)-HODE
(43) 13(R)-HODE
(44) 13(S)-HODE
(45) Leukotriene B$_4$
(46) 6-trans Leukotriene B$_4$
(47) 6trans-12-epi Leukotriene B$_4$
(48) 6, 7-dihydro Leukotriene B$_4$
(49) 12-keto Leukotriene B$_4$
(50) 18-carboxy dinor Leukotriene B$_4$
(51) 20-carboxy Leukotriene B$_4$
(52) 20-hydroxy Leukotriene B$_4$
(53) 20-trifluoro Leukotriene B$_4$
(54) Leukotriene B$_5$ Briefly, FIG. 8 shows a reaction scheme in which a transenal derived from a 2-deoxypyranose derivative by ylide-induced β-elimination was exploited for the synthesis and stereochemical revision of a novel eicosanoid, a derivative of fatty acid containing an α, β-dihydro-diene subunit. The reaction scheme shows methyl pyranoside, 36, obtained as an anomeric mixture in 2 steps from 2deoxy-D-galactose, was converted to aldehyde, 39, by successive benzoylation of the secondary alcohols, zinc bromide mediated detritylation, and pyridinium dichromate (PDC) oxidation. Elaboration of 39 with hexylidenetriphenylphosphorane generated at 0° C. in THF using sodium bis (trimethylsilyl)amide, followed by exposure to excess trimethylsilyl iodide afforded lactol, 43. The key transformation, i.e., the "one pot" construction of the Z,E-diene, exploits the facile, ylide-induced elimination of benzoate from the open-chain tautomer of 43 under the conditions used for Wittig olefination. Preferential condensation in situ of the resultant trans-enal with 7-carbomethoxyhepta-3(Z)-en-1-ylidenetriphenylphosphorane furnished benzoate, 45, and its transesterification product, 46, as an 1:1 mixture in good yield after chromatographic purification. Solvolysis (NaOMe, MeOH) of 45 and 46 gave rise to the same diol which upon acetylation yielded its respective acetate. Mitsunobu inversion (Mitsunobu, O., (1981) *Synthesis*: 1–28) of 45 and 46 using diethyl azodicarboxylate/triphenylphosphine/chloroacetic acid in THF at room temperature led to 47 and 48, respectively. Removal of the protecting group by NaOMe, MeOH, followed by acetylation yielded the acetates 50 and 51, respectively.

FIG. 8 shows the following examples:

EXAMPLE 12

The diol, 36, 1.23 g was dissolved in a mixture of 12 ml of dichloromethane: pyridine (5:1). Benzoyl chloride (1.4 ml, 4 equiv.) was added dropwise into the solution. The resulting mixture was stirred at room temperature for 4 hours and diluted with dichloromethane (100 ml), washed with saturated aqueous CuSO$_4$ (3×100 ml), water and brine, successively. The organic phase was dried over anhydrous sodium sulfate and then filtered. The solvent was removed at reduced pressure to give the crude product, 37.

R$_f$=0.44 with ethyl acetate: hexane (1:2).

EXAMPLE 13

The crude trityl, 37, was dissolved in 30 ml of dichloromethane to which was added a solution of zinc bromide (2 g, 3 equiv.) in methanol (3 ml), dropwise. The resulting mixture was stirred for 1 hour at room temperature and workup with aqueous buffer (PH=7). The mixture was extracted with dichloromethane, the combined organic extracts were dried over anhydrous sodium sulfate and then filtered. The solvent was removed at reduced pressure and chromatography of the residue with dichloromethane with increasing amounts of methanol (up to 5%) gave the product 38 (838 mg) in a total yield of 75% for the two reactions above.

$R_f$=0.33 in ethyl acetate: hexane (1:1).

EXAMPLE 14

The alcohol 38 (320 mg) was dissolved in 20 ml of dichloromethane and then pyridinium dichromate (470 mg, 1.5 equiv.) was added, followed by 800 mg of freshly activated molecular sieves (3 angstrom). The resulting mixture was stirred for 1 hour at room temperature and diluted with ether (100 ml). The reaction mixture was filtered through a short silica gel column and the solvent was removed at reduced pressure to give the crude aldehyde, 39.

$R_f$=0.32 in ethyl acetate: hexane (1:1).

EXAMPLE 15

To a suspension of hexytriphenylphosphonium bromide, 40, (810 mg, 2 equiv.) in 10 ml of THF, 1.7 ml of $(Me_3Si)_2NNa$ (1M) was added dropwise at 0° C. and the reaction mixture was stirred for 30 minutes at 0° C. to form an orange solution. The solution was cooled to −78° C. and to it was added 30 ml of toluene, then continued the stirring for 20 minutes. A solution of the above crude aldehyde, 39, in a minimal amount of toluene was added, and the mixture was stirred at −78° C. for 30 minutes. Workup with 50% aqueous $NH_4OAC$. The resulting mixture was extracted with ethyl acetate. The combined organic extracts were dried over anhydrous sodium sulfate and filtered. The solvent was removed at reduced pressure. Chromatography of the residue with 20% ethyl acetate in hexane gave the product 41 (210 mg) in 56% yield for the above two reactions.

$R_f$=0.61 in ethyl acetate:hexane (1:2).

EXAMPLE 16

Sodium iodide (690 mg, 10 equiv.) was dissolved in 8 ml of acetonitrile and the mixture was cooled to 0° C. Then $Me_3SiCl$ (600 μl, 10 equiv.) was added to the mixture and was stirred for 10 minutes. A solution of the ether, 41, (210 mg, 0.46 mmol) in a minimal amount of acetonitrile was added, and the reaction mixture was stirred at 0° C. for 1 hour. Workup with saturated aqueous sodium bicarbonate. The resulting mixture was extracted with ether. The combined organic phases were washed with saturated aqueous sodium thiosulfate, 5% sodium bicarbonate water, and brine, successively, then dried over anhydrous sodium sulfate. After filtration, the filtrate was concentrated at reduced pressure. Chromatography of the residue with 20% ethyl acetate in hexane gave the product 43 (180 mg) in 89% yield.

$R_f$=0.41 in ethyl acetate:hexane (1:2).

EXAMPLE 17

The 7-carbomethoxyhepta-3(Z)-en-triphenylphosphonium bromide, 44, (450 mg, 4 equiv.) was dissolved in 10 ml of THF containing 1 ml of HMPA, then cooled to −40° C. Then $(Me_3Si)_2NNa$ (1M, 800 μl) was added dropwise and the solution was stirred for 30 minutes at the same temperature. A solution of the lactol, 43, (86 mg) in a minimal amount of THF was added and the reaction mixture was stirred at −40° C. for 1 hour. Workup with saturated aqueous $NH_4Cl$. The resulting mixture was extracted with ethyl acetate. The combined organic extracts were dried over anhydrous sodium sulfate and filtered. The solvent was removed under reduced pressure. Chromatography of the residue with 10% ethyl acetate in hexane gave the product 45 (32 mg) and its transesterification product, 46, (32 mg) in a total yield of 73%.

$R_f$(45)=0.32 in ethyl acetate:hexane (1:4).
$R_f$(46)=0.38 in ethyl acetate:hexane (1:4).

EXAMPLE 18

The alcohol, 45, (16 mg, 0.035 mmol) was dissolved in 4 ml of THF. Triphenylphosphine (37 mg, 4 equiv.), chloroacetic acid (13 mg, 4 equiv.) and diethyl azodicarboxylate (22 μl, 4 equiv.) were then added successively. The reaction mixture was stirred for 10 minutes and the solvent was removed under reduced pressure. TLC of the residue with 10% ethyl acetate in hexane gave the product 47 (14 mg) in 76% yield.

$R_f$=0.45 with ethyl acetate:hexane (1:4).

EXAMPLE 19

The ester, 47, (14 mg, 0.026 mmol) was dissolved in 2 ml of methanol to which was added sodium methoxide (5.4M, 20 μl, 4 equiv.) at 0° C. The mixture solution was stirred at room temperature for 2 hours, then cooled to 0° C. again. Then 3N HCl was added dropwise to neutralize the mixture to pH=7. Solvent was removed at reduced pressure. The crude product was dried under vacuum, then dichloromethane (2 ml), pyridine (200 μl), acetic anhydride (12 μl), and a catalytic amount of 4-dimethylaminopyridine were added successively. The reaction mixture was stirred for 2 hours and then diluted with dichloromethane. The resulting mixture was washed with saturated aqueous $CuSO_4$, water and brine, successively. The combined organic phase was dried over anhydrous sodium sulfate and filtered. Solvent was removed at reduced pressure and TLC of the residue with 10% ethyl acetate in hexane gave the product 50 (8.3 mg) in 75% yield.

$R_f$=0.71 with ethyl acetate:hexane (1:4).

EXAMPLE 20

The alcohol, 46, (25 mg) was dissolved in 6 ml of THF. Triphenylphosphine (58 mg, 4 equiv.), chloroacetic acid (20 mg, 4 equiv.) and diethyl azodicarboxylate (34 μl, 4 equiv.) were then added successively. The reaction mixture was stirred for 10 minutes and the solvent was removed under reduced pressure. TLC of the residue with 10% ethyl acetate in hexane gave the product 48 (20 mg) in 69% yield.

$R_f$=0.45 with ethyl acetate:hexane (1:4).

EXAMPLE 21

The ester, 48, (20 mg) was dissolved in 2 ml of methanol to which was added sodium methoxide (5.4 m, 28 μl, 4 equiv.) at 0° C. The mixture solution was stirred at room temperature for 2 hours, then cooled to 0° C. again. Then 3N HCl was added dropwise to neutralize the mixture to pH=7. Solvent was removed at reduced pressure. The crude product was dried under vacuum, then dichloromethane (3 ml), pyridine (300 μl), acetic anhydride (17 μl), and a catalytic amount of 4-dimethylaminopyridine were added successively. The reaction mixture was stirred for 2 hours and then diluted with dichloromethane. The resulting mixture was washed with saturated aqueous $CuSO_4$, water and brine, successively. The combined organic phase was dried over anhydrous sodium sulfate and filtered. Solvent was removed at reduced pressure and TLC of the residue with 10% ethyl acetate in hexane gave the product 51 (12 mg) in 75% yield.

$R_f = 0.71$ with ethyl acetate:hexane (1:4).

EXAMPLE 22

Compounds which can be formed in a manner analogous to the procedures described in the previous examples using appropriate starting materials:
(1) 5(R), 6(R)-DiHETE
(2) 5(S), 6(S)-DiHETE
(3) 5(R), 6(S)-DiHETE
(4) 5(S), 6(R)-DiHETE
(5) Lipoxin $A_4$
(6) Lipoxin $B_4$
(7) Leukotriene $A_3$
(8) Leukotriene $A_4$
(9) 20-trifluoro Leukotriene $A_4$
(10) Leukotriene $A_5$
(11) Leukotriene $C_4$
(12) Leukotriene $C_5$
(13) Leukotriene $D_4$
(14) Leukotriene $D_5$
(15) Leukotriene $E_4$
(16) N-acetyl Leukotriene $E_4$
(17) 14-carboxy hexanor Leukotriene $E_4$
(18) N-acetyl-14-carboxy hexanor Leukotriene $E_4$
(19) 16-carboxy-$\Delta^{13}$-tetranor Leukotriene $E_4$
(20) N-acetyl-16-carboxy-$\Delta^{13}$-tetranor Leukotriene $E_4$
(21) 16-carboxy-14,15-dihydro tetranor Leukotriene $E_4$
(22) N-acetyl-16-carboxy-14,15-dihydro tetranor Leukotriene $E_4$
(23) 18-carboxy dinor Leukotriene $E_4$
(24) N-acetyl-18-carboxy dinor Leukotriene $E_4$
(25) 20-carboxy Leukotriene $E_4$
(26) N-acetyl-20-carboxy Leukotriene $E_4$
(27) 20-trifluoro Leukotriene $E_4$
(28) Leukotriene $E_5$
(29) Leukotriene $F_4$ The invention now being fully described, it will be apparent to one of ordinary skill in the art that many changes and modifications can be made thereto without departing from the spirit or scope of the invention as defined in the following claims.

I claim:

1. A process for functionalizing a carbohydrate derivative comprising:
   coupling a first substituted and protected carbohydrate derivative with a first coupling reagent to yield a second substituted and protected carbohydrate derivative;
   deprotecting said second substituted and protected carbohydrate derivative to yield a substituted and deprotected carbohydrate derivative, said substituted and deprotected carbohydrate derivative being characterized as having a free hydroxyl group at its C-1 position; and
   coupling said substituted and deprotected carbohydrate derivative with a second coupling reagent, thereby effecting a base-induced $\beta$-elimination and subsequent olefination to form a compound containing a subunit having at least one hydroxyl group and a diene group.

2. A process according to claim 1, wherein the first substituted and protected carbohydrate derivative is a derivative of 2-deoxycarbohydrate having a C-1 hydroxyl group protected by a methyl group and at least one other hydroxyl group protected by an ester group.

3. A process according to claim 1, wherein said first coupling reagent is an organocopper reagent.

4. A process according to claim 1, wherein said second coupling reagent is a Wittig reagent.

5. A process according to claim 1 further comprising the step of hydrolysis.

6. A process for functionalizing a 2-deoxyfuranose derivative comprising:
   coupling a first substituted and protected 2-deoxyfuranose derivative with a first coupling reagent to yield a second substituted and protected 2-deoxyfuranose derivative;
   deprotecting said second substituted and protected 2-deoxyfuranose derivative to yield a substituted and deprotected 2-deoxyfuranose derivative, said substituted and deprotected 2-deoxyfuranose being characterized as having a free hydroxyl group at its C-1 position; and
   coupling said substituted and deprotected 2-deoxyfuranose derivative with a second coupling reagent, thereby effecting a base-induced $\beta$-elimination and subsequent olefination to form a derivative of $\alpha$-hydroxy-diene fatty acid.

7. A process according to claim 6, wherein the first substituted and protected 2-deoxyfuranose derivative has a C-1 hydroxyl group protected by a methyl group and a C-3 hydroxyl group protected by an ester group.

8. A process according to claim 6, wherein said first coupling reagent is an organocopper reagent.

9. A process according to claim 6, wherein said second coupling reagent is a Wittig reagent.

10. A process according to claim 6 further comprising the step of hydrolysis.

11. A process for functionalizing a 2-deoxypyranose derivative comprising:
    coupling a first substituted and protected 2-deoxypyranose derivative with a first coupling reagent to yield a second substituted and protected 2-deoxypyranose derivative;
    deprotecting said second substituted and protected 2-deoxypyranose derivative to yield a substituted and deprotected 2-deoxypyranose derivative, said substituted and deprotected 2-deoxypyranose being characterized as having a free hydroxyl group at its C-1 position; and
    coupling said substituted and deprotected 2-deoxypyranose derivative with a second coupling reagent, thereby effecting a base-induced $\beta$-elimination and subsequent olefination to form a derivative of an $\alpha,\beta$-dihydroxy-diene fatty acid.

12. A process according to claim 11, wherein the first substituted and protected 2-deoxypyranose derivative has a C-1 hydroxyl group protected by a methyl group, at least a C-3 hydroxyl group protected by an ester group, and a C-6 hydroxyl group protected by an acid labile group.

13. A process according to claim 11, wherein said first coupling reagent is a Wittig reagent.

14. A process according to claim 11, wherein said second coupling reagent is a Wittig reagent.

15. A process according to claim 11 further comprising the step of hydrolysis.

16. A process for the preparation of a derivative of fatty acid containing a subunit having at least one hydroxyl group and a diene group comprising:

coupling a first substituted and protected carbohydrate derivative with a first coupling reagent to yield a second substituted and protected carbohydrate derivative;

deprotecting said second substituted and protected carbohydrate derivative to yield a substituted and deprotected carbohydrate derivative, said substituted and deprotected carbohydrate derivative being characterized as having a free hydroxyl group at its C-1 position; and coupling said substituted and deprotected carbohydrate derivative with a second coupling reagent, thereby effecting a base-induced $\beta$-elimination and subsequent olefination.

17. A process for the preparation of a derivative of fatty acid containing an $\alpha$-hydroxy-diene subunit comprising:

coupling a first substituted and protected 2-deoxyfuranose derivative with a first coupling reagent to yield a second substituted and protected 2-deoxyfuranose derivative;

deprotecting said second substituted and protected 2-deoxyfuranose derivative to yield a substituted and deprotected 2-deoxyfuranose derivative, said substituted and deprotected 2-deoxyfuranose derivative being characterized as having a free hydroxyl group at its C-1 position; and coupling said substituted and deprotected 2-deoxyfuranose derivative with a second coupling reagent, thereby effecting a base-induced $\beta$-elimination and subsequent olefination.

18. A process for the preparation of a derivative of fatty acid containing an $\alpha$, $\beta$-dihydroxy-diene subunit comprising:

coupling a first substituted and protected 2-deoxypyranose derivative with a first coupling reagent to yield a second substituted and protected 2-deoxypyranose derivative;

deprotecting said second substituted and protected 2-deoxypyranose derivative to yield a substituted and deprotected 2-deoxypyranose derivative, said substituted and deprotected 2-deoxypyranose derivative being characterized as having a free hydroxyl group at its C-1 position; and coupling said substituted and deprotected 2-deoxypyranose derivative with a second coupling reagent, thereby effecting a base-induced $\beta$-elimination and subsequent olefination.

19. A process for the preparation of a derivative of fatty acid containing a subunit having at least one hydroxyl group and a diene group comprising:

coupling a substituted carbohydrate derivative, having a first free hydroxyl group at its C-1 position, with a first coupling reagent to yield a substituted diene derivative having a second free hydroxyl group generated from ring opening of said substituted carbohydrate derivative;

protecting said second free hydroxyl group in said substituted diene derivative to yield a substituted and protected diene derivative;

coupling said substituted and protected diene derivative with a second coupling reagent, thereby effecting a base-induced $\beta$-elimination and subsequent olefination to form a protected precursor; and deprotecting said protected precursor.

20. A process according to claim 19, wherein the first substituted carbohydrate derivative is a derivative of 2-deoxyfuranose having a free C-1 hydroxyl group.

21. A process according to claim 19, wherein said first substituted carbohydrate derivative is a derivative of 2-deoxypyranose having a free C-1 hydroxyl group.

22. A process for functionalizing a carbohydrate derivative comprising:

coupling a substituted carbohydrate derivative, having a first free hydroxyl group at its C-1 position, with a first coupling reagent to yield a substituted diene derivative having a second free hydroxyl group generated from ring opening of said substituted carbohydrate derivative;

protecting said second free hydroxyl group in said substituted diene derivative to yield a substituted and protected diene derivative;

coupling said substituted and protected diene derivative with a second coupling reagent, thereby effecting a base-induced $\beta$-elimination and subsequent olefination to form a protected precursor; and deprotecting said protected precursor to give a compound containing a subunit having at least one free hydroxyl group and a diene group.

23. A process according to claim 22, wherein the first substituted carbohydrate derivative is a derivative of 2-deoxyfuranose having a free C-1 hydroxyl group.

24. A process according to claim 22, wherein said first substituted carbohydrate derivative is a derivative of 2-deoxypyranose having a free C-1 hydroxyl group.

* * * * *

UNITED STATES PATENT AND TRADEMARK OFFICE
CERTIFICATE OF CORRECTION

PATENT NO. : 5,334,736
DATED : August 2, 1994
INVENTOR(S) : Sun, Lumin et al.

It is certified that error appears in the above-indentified patent and that said Letters Patent is hereby corrected as shown below:

Title Page, item [54]   Replace "$\beta$-ELIMINATIOM"
With --$\beta$-ELIMINATION--

Column 1, line 4   Replace "$\beta$-ELIMINATIOM"
With --$\beta$-ELIMINATION--

Column 2, line 62   Replace "See"
With --_See_--

Column 7, line 39   Replace "BrPh$_3$C$_6$H$_{13}$,"
With --BrPh$_3$PC$_6$H$_{13}$,--

Column 7, line 51   Replace "2-deoxypyranose;"
With --2-deoxypyranose,"

Column 10, line 30   Replace "produce,"
With --product,--

Signed and Sealed this

Twenty-eighth Day of May, 1996

Attest:

BRUCE LEHMAN

*Attesting Officer*   *Commissioner of Patents and Trademarks*